United States Patent [19]

Lown et al.

[11] Patent Number: 4,912,199
[45] Date of Patent: Mar. 27, 1990

[54] OLIGOPEPTIDE ANTICANCER AND ANTIVIRAL AGENTS

[75] Inventors: J. William Lown; Krzysztof Krowicki, both of Edmonton, Canada

[73] Assignee: The Governors of the University of Alberta, Edmonton, Canada

[21] Appl. No.: 73,725

[22] Filed: Jul. 15, 1987

[51] Int. Cl.$^4$ .................... C07C 103/52; C07K 7/06; A61K 37/00
[52] U.S. Cl. ................................. 530/331; 530/329; 530/330; 514/18; 514/19
[58] Field of Search ............................... 530/329-331; 514/18-19

[56] References Cited

U.S. PATENT DOCUMENTS

| | | | |
|---|---|---|---|
| 4,216,208 | 8/1980 | De Barbieri . | |
| 4,314,999 | 2/1982 | De Barbieri . | |
| 4,454,065 | 6/1984 | Gilvarg et al. . | |
| 4,483,850 | 11/1984 | Patchett et al. . | |
| 4,540,683 | 9/1985 | DeBarbieri et al. | 514/18 |

FOREIGN PATENT DOCUMENTS

WO86/05518 3/1986 PCT Int'l Appl. .
WO86/05519 3/1986 PCT Int'l Appl. .

OTHER PUBLICATIONS

Lown et al., "Molecular Recognition between Oligopeptides and Nucleic Acids: Novel Imidazole-Containing Oligopeptides Related to Netropsin that Exhibit Altered DNA Sequence Specificity," Biochemistry, vol., 25, pp. 7408-7416, 1986.
Martin et al., "Mechanisms of Antiviral Immunity Induced by Vaccinia Virus Recombinant Expressing Herpes Simplex Virus Type 1 Glyroprote D: Cytotoxic T Cells", Journal of Virology, vol. 61, pp. 726-734, 1987.
Lown et al., "Structure-Activity Relationship of Novel Oligopeptide Antiviral and Antitumor Agents Related to Netropsin and Distamycin," J. Med. Chem. vol. 29, pp. 1210-1214, 1986.
Lown et al., "Efficient Total Synthesis of the Oligopeptide Antibiotics Netropsin and Distamycin", J. Org. Chem. vol. 50, pp. 3774-3779, 1985.
*Efficient Total Syntheses of the Oligopeptide Antibiotics Netropsin and Distamycin,* Lown and Krowicki, American Chemical Society, J. Org. Chem., vol. 50, No. 20, 1985, pp. 3774-3779.
Youngquist et al., "Sequence-Specific Recognition of B-DNA by Oligo(N-Methylpyrrolecarboxamide)s," Proc. Natl. Acad. Sci. U.S.A. (1985), 82:2565-2569.

*Primary Examiner*—Margaret Moskowitz
*Assistant Examiner*—Abdel A. Mohamed
*Attorney, Agent, or Firm*—Banner, Birch, McKie & Beckett

[57] ABSTRACT

Oligopeptide anticancer and antiviral agents are represented by the formula:

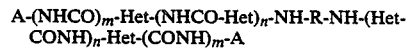

A-(NHCO)$_m$-Het-(NHCO-Het)$_n$-NH-R-NH-(Het-CONH)$_n$-Het-(CONH)$_m$-A wherein A is a moiety bearing a positive charge and of a size which avoids steric inhibition of binding of said compound to deoxyribonucleic acid sequence; R is a moiety derived from a dicarboxylic acid; Het is a five-membered heterocyclic moiety; n is 1, 2 or 3, m is 0 or 1. These compounds exhibit antiviral activity especially against herpes simplex I and II, vaccinia viruses and anticancer activity against several animal and human tumor lines.

37 Claims, 2 Drawing Sheets

OLIGOPEPTIDE ANTICANCER AND ANTIVIRAL AGENTS

FIELD OF THE INVENTION

This invention relates to oligopeptides which are particularly useful as anticancer and antiviral agents.

BACKGROUND OF THE INVENTION

Various oligopeptide derivatives have demonstrated various medicinal uses, such as enzyme inhibitors as disclosed in U.S. Pat. No. 4,483,850. It is also known that various oligopeptides have anti-tumor activity as disclosed in U.S. Pat. Nos. 4,216,208 and 4,314,999. Antibiotic activity of oligopeptides is disclosed in U.S. Pat. No. 4,454,065. Naturally occurring oligopeptides, netropsin and distamycin, have been discovered as having antiviral and anti-tumor activity. The chemical formulas for netropsin and distamycin are as follows:

These oligopeptides are disclosed in Julia, M., Préau-Joseph, N., C. R. Hebd-Seances, *Acad. Sci.* 1963, 257. 1115 and Arcamone, F.; Orezzi, P. G.; Barbier, W.; Nicolella, V.; Penco, S.; *Gazz. Chim. Ital.*, 1967, 97, 1097.

Netropsin and distamycin contain pyrrole moieties connected by peptide bonds and with side chains, at least one of which is positively charged; i.e., an amidine group, or a group of the guanidyl type.

Only distamycin has been used as a therapeutic agent as commercialized and sold under the trade mark STALLIMYCIN HYDROCHLORIDE in the form a 1% cream, ointment or paste. This composition has been used in the treatments of infections produced by herpes simplex, herpes zoster and vaccinia viruses. Topical application of distamycin has been limited due to its high cytotoxicity and a low therapeutic index which in the instance of treating the herpes virus is about 3.

According to this invention oligopeptides containing pyrrole moieties have been developed which have significantly enhanced antiviral and anticancer activity compared to prior types of oligopeptides.

SUMMARY OF THE INVENTION

According to an aspect of the invention, a compound represented by the formula I:

wherein A is a moiety bearing a positive charge and of a size which avoids steric inhibition of binding of said compound to deoxyribonucleic acid sequences; R is a moiety derived from a dicarboxylic acid; Het is a five-membered heterocyclic moiety; n is 1, 2 or 3, m is 0 or 1 and pharmaceutically acceptable salts thereof.

According to a preferred aspect of the invention, such compounds exhibit antiviral and anti-tumor acitivity especially against herpes simplex I and II, vaccinia viruses and anticancer activity against several animal and human tumor lines, including L 1210; P 388; FM3A, Raji; Molt/4F and Namalva hepatoma.

According to another aspect of the invention, a process for preparing such compounds comprises reacting a compound of the formula:

wherein m and n are as defined above; and B is the same as A or is a group with a nitrile, halogen or sulfide substituent; with a dicarboxylic acid of the formula:

wherein R is as defined above and X is halogen, imidazolide or other reactive moiety and converting B to A to form said moiety bearing a positive charge.

BRIEF DESCRIPTION OF THE DRAWINGS

Preferred embodiments of the invention are demonstrated with respect to the drawings wherein.

DETAILED DESCRIPTION OF THE PREFERRED EMBODIMENTS

Compounds according to this invention demonstrate significant anticancer and antiviral activity. Although the actual biological mechanism of these compounds which precipitate antiviral and anti-tumor activity is not fully understood, it is thought that the activity is due to the compounds of this invention binding with deoxyribonucleic acid sequence(s) (DNA) of the target biological matter to inactivate such DNA which codes for the viral and tumor activity. The compounds of this invention have heterocyclic moieties which may be the same or different linked by a dicarboxylic acid derivative. Such linked heterocyclic moieties of this invention have significant unexpected activity compared to unlinked pyrrole moieties such as the naturally occurring netropsin and distamycin.

The compounds according to this invention are represented by the following formula:

wherein A is a moiety bearing a positive charge and of a size which avoids steric inhibition binding of said compound to deoxyribonucleic acid sequences; R is a moiety derived from a dicarboxylic acid; Het is a five-membered heterocyclic moiety; n is 1, 2 or 3, m is 0 or 1 and pharmaceutically acceptable salts thereof.

The positive charged moiety at each extremity of the compound and identified as group A may be selected from the group of derivatives consisting of an amidine, a guanidine, secondary ammonium salts, tertiary ammonium salts, quaternary ammonium salts, sulfonium salts and phosphonium salts.

The selected amidine may have one or both nitrogen atoms of the amidine as a member of a five-membered cyclic structure. More particularly, the amidine derivative is represented by the formula:

where p equals 0 to 5 and X is —H, —OH, —NH$_2$, —CH$_3$, —C$_2$H$_5$, —C$_3$H$_7$.

The selected guanidine for substituent A may be represented by the formula:

where p equals 0 to 5 and X equals —H, —OH, —NH$_2$, —CH$_3$, —C$_2$H$_5$, —C$_3$H$_7$.

When A is selected to be a quaternary, tertiary or secondary ammonium salt, it may be represented by the formula:

where p equals 1 to 5 and q equals 0 to 3 and X is an alkyl or alkenyl group of 1 to 3 carbon atoms.

When A is selected as a sulfonium salt, it may be represented by the formula:

where p equals 0 to 5 and X are alkyl or alkenyl groups of 1 to 3 carbon atoms.

In the heterocyclic moieties, Het may be the same in each moiety or may be different. Preferably, the Het group is selected from the group consisting of a pyrrole, an imidazole, a triazole, a pyrazole, a thiazole, a thiophane, a furan, an oxazole and derivatives thereof.

Preferred Het substituents are N-alkyl pyrrole having 1 to 6 carbon atoms in the alkyl group; N-alkyl imidazole having 1 to 6 carbon atoms in the alkyl group and alkyl pyrazole having 1 to 6 carbon atoms in the alkyl group and alkyl triazol having 1 to 6 carbon atoms in the alkyl group. Preferably the N-alkyl pyrrole has 1 to 4 carbon atoms in the alkyl group.

The linking group is a derivative from carboxylic acid. R is represented generally by the formula:

where p equals any number from 1 to 16. Alternatively, R may be a residue of carbonic acid, namely, or R may be a residue of an aromatic dicarboxylic acid.

Other alternative structures for the linking group may be a residue of an unsaturated aliphatic dicarboxylic acid of the formula:

where p equals any number from 2 to 16.

R may also be a residue of cycloalkane dicarboxylic acids of the formula:

where p equals any number from 3 to 7.

R may also be a residue of a cycloalkene dicarboxylic acid of the formula:

where p equals any number from 5 to 7.

Preferred compounds include compounds of formula I wherein Het is pyrrole and m is 1; A is:

and R is —CO—(CH$_2$)$_l$—CO— where l may range between 0 to 8.

The heterocyclic moiety of the compounds of this invention may be linked in accordance with various processes by use of the dicarboxylic acid derivatives. In accordance with an aspect of this invention, the process for providing such linkage comprises reacting a compound of the formula:

B-(NHCO)$_m$-Het-(NHCO-Het)$_n$-NH$_2$ wherein m and n are as defined above; and B is the same as A or is a group with a nitrile, halogen or sulfide substituent; with a dicarboxylic acid of the formula:

X-R-X wherein R is as defined above and X is halogen, imidazolide or other reactive moiety and converting B to A to form said moiety bearing a positive charge.

In the reactants, B may be generally represented by the formula:

end group. In that instance, B has the general formula:

wherein X is an alkyl or alkenyl group having 1 to 3 carbon atoms and p equals 0 to 5 and s equals 0 or 1.

According to preferred embodiments of the invention, the following reaction schemes demonstrate preferred chemical pathways to the compounds of this invention having the various desired end groups:

A - Preparation of Amidinium End Group

B - Preparation of Guanidinium End Groups

[Figure continues with preparation schemes C and D]

C - Preparation of Ammonium Salt in End Group

2Cl—C$_p$H$_{2p}$—(NHCO)$_m$—Het—(NHCO—Het)$_n$—NH$_2$ + Cl—R—Cl $\xrightarrow{iPr_2EtN}$

[Cl—C$_p$H$_{2p}$—(NHCO)$_m$—Het—(NHCO—Het)$_n$—NH$\frac{1}{2}$R $\xrightarrow{HNH_qX_{(3-q)}}$

[X$_{(3-q)}^+$NH$_q$—C$_p$H$_{2p}$—(NHCO)$_m$—Het—(NHCO—Het)—NH$\frac{1}{2}$R

D - Preparation of Sulfonium Salts

2XS—C$_p$H$_{2p}$—(NHCO)$_m$—Het—NHCO—Het)$_n$—NH$_2$ + Cl—R—Cl $\xrightarrow{iPr_2EtN}$

[XS—C$_p$H$_{2p}$—(NHCO)$_m$—Het—(NH—CO—Het)$_n$—NH$\frac{1}{2}$R $\xrightarrow{YCl\ (or\ Br)}$

[XYS$^+$—C$_p$H$_{2p}$—(NHCO)$_m$—Het—(NHCO—Het)$_n$—NH$\frac{1}{2}$R

Z-C$_p$H$_{2p}$- wherein Z is CN—, hal or XS; hal is a halogen ion, X is an alkyl or alkenyl group having 1 to 3 carbon atoms, and p equals 0 to 5.

It is appreciated that B may also be identical to A in providing a charged group, for example, a guanidinium Reference may be made to J. W. Lown and K. Krowicki, *J. Org. Chem.* 1985, 50, 3774 regarding the synthesis of related types of pyrrole moieties such as the synthesis of distamycin. The general synthesis of the compounds according to this invention are based on the total synthesis of distamycin. Dipyrrole or tripyrrole peptides bearing an amino group and a side-chain containing a group (B) which is the nitrile, ammonium or sulfide as represented by the following formula:

r = 2,3 are allowed to react with a dicarboxylic acid dichloride in the presence of a base or with a diimidazolide of a dicarboxylic acid to give a bis-amide of the dicarboxylic acid. The resulting compound in the case of nitrile is allowed to react with ethanol in the presence of hydrochloric acid and then with ammonia (Pinner reaction) to generate the amidinium moiety in the final product, as exemplified by the above reaction scheme A. As with reaction scheme D, the sulfide is methalyted to produce the corresponding sulfonium salt. Preferred embodiments of the invention are exemplified in the following Examples which are in no way to be construed as limiting the scope of the appended claims.

EXAMPLE 1

Compound of the formula I, where n=1, m=1;

R equals —$COCH_2CH_2CO$— is prepared. 1-Methyl-4-(1-methyl-4-aminopyrrole-2-carboxamido)-pyrrole-2-carboxamidopropionitrile (105 mg, 0.33 mmole) and i-$Pr_2EtN$ (diisopropylethylamine) (65 μl, 0.37 mmole) are dissolved in anhydrous acetonitrile (5 ml) and cooled to −20° C. Succinyl chloride (18 μl, 0.16 mmole) in anhydrous THF (1 ml) is added and the mixture is allowed to reach room temperature. The solvents are evaporated to dryness and water added. The resulting solid is collected and washed with hot MeOH to give 90 mg (77% yield) of the product m.p. 297° C. The latter is suspended in anhydrous EtOH and saturated with HCl while cooling. After 1.5 hours at room temperature, the solvent is removed in vacuo and the residue is washed with dry ether then ethanol is added followed by some ammonia condensed into the solution. After 1 hour at room temperature, the solvent is removed in vacuo and the residue is washed with MeOH, EtOH and hexane to afford 80 mg of a solid. Recrystallization from a small volume of water gives a jelly-like precipitate which is washed with EtOH, hexane and dried to give 35 mg (35% yield) of pure product m.p. 283°–285° C. dec. $^1$H-NMR (DMSO-$d_6$): δ 2.60 (m, 4H), 3.60 (m, 6.92 (d, 2H), 7.18 (d, 2H), 8.25 (t, 1H), 8.70 (bs, 2H), 9.02 (bs, 2H), 9.93 and 9.97 (2s, 2H), MS-FAB (m/z): 745 (M-Cl-HCl)+: Anal. Calcd. for $C_{34}H_{46}Cl_2N_{14}O_6$: C, 49.9, H, 5.7, N, 24.0, Cl, 8.7, Found: C, 50.3, H, 6.05, N, 22.9, Cl, 8.7.

EXAMPLE 2

Compound of the formula I, where n equals 1; m=1

R equals —CO— is prepared. 1-Methyl-4-(1-methyl-4-aminopyrrole-2-carboxamido)-pyrrole-2-carboxamidopropionitrile (315 mg, 1 mmole) and 81 mg of 1,1'-carbonyldiimidazole are dissolve in 10 ml of anhydrous $CH_3CN$ and refluxed under argon for 5 minutes. A solid forms which is collected to give 302 mg (88.6% yield) of the pure product which is treated with HCl in EtOH and then $NH_3$ (as in Example 1). After the reaction is completed, the mixture is decanted from an insoluble residue. The solvent is removed in vacuo and the residue is dissolved in 4 ml of MeOH and an excess of $CH_3CN$ is added to precipitate the product which is collected and washed with 1 ml of cold water whereupon it becomes jelly-like. The product is redissolved in MeOH and reprecipitated with $CH_3CN$ to give 216 mg (57% overall yield) of the pure compound m.p. 211°–215° C.; $^1$H-NMR (DMSO-$d_6$): δ 2.64 (t, 2H), 3.52 (q, 2H), 3.84 (s, 6H), 6.82, 6.94, 7.03, 7.20 (4d, 4H), 8.25 (t, 1H), 8.73 (2s, 3H), 9.05 (s, 2H), 9.88 (s, 1H), MS-FAB: 690 (M-Cl-HCl)+. Anal. Calcd. for $C_{31}H_{42}Cl_2N_{14}O_5$: C, 48.9, H, 5.6, Cl, 9.3, N, 25.7; Found: C, 48.5, H, 5.7, Cl, 9.7, N, 25.3.

EXAMPLES 3(A) AND (B)

The following Examples illustrate the effect of altering the steric size of the terminal group (in these cases trialkylammonium) on the basic Het block of the general title formula on the DNA binding and antiviral efficacy.

(A)

1-Methyl-4-(1-methyl-4-trimethylammonium-acetamidopyrrole-2-carboxamido)pyrrole-2-carboxamidopropionamidine chloride hydrochloride A solution of the precursor 1-methyl-4-(1-methyl-4-trimethylammonium-acetamido-pyrrole-2-carboxamido)pyrrole-2-carboxamidopropionitrile chloride (347 mg, 0.07 mmoles) in 5 ml of absolute ethanol was treated with dry hydrogen chloride with cooling. After 2 hours, the solvent was removed in vacuo, 5 ml of absolute ethanol was added and dry $NH_3$ gas passed into the solution. The solid dissolved during 2 hours at room temperature, then the solution was evaporated to dryness and extracted with hot isopropyl alcohol (100 ml). The extract was concentrated to ca. 10 ml, acetone added and the resulting precipitate collected, washed with acetone, and dried in vacuo to give the product, 300 mg (85% yield) as an amorphous hygroscopic solid, no definite m.p.; $^1$H-NMR (DMSO-$d_6$): δ2.67 (t, 2H), 3.31 (s, 9H) 3.52 (q, 2H), 3.82 and 3.87 (2s, 6H), 4.44 (s, 2H), 6.97 (d, 1H), 7.02 (d, 1H), 7.24 (d, 1H), 7.29 (d, 1H), 8.31 (t, 1H), 8.82 (bs, 2H), 9.72 (bs, 2H), 10.06 (s, 1H), 11.23 (s, 1H): IR (Nujol) $v_{max}$: 1260, 1377, 1405, 1453, 1531, 1582, 1643, 1685, 3247 cm$^{-1}$; MS-FAB (m/z) 430 (M-HCl-Cl)+.

Sulfate

The sulfate corresponding to the product was prepared in order to obtain an analytically pure sample by precipitation from a methanolic solution of the above compound by means of a large excess of tetraethylammonium sulfate, m.p. 295° C.: IR (Nujol) $v_{max}$: 1255, 1377, 1405, 1462, 1525, 1560, 1580, 1640, 1670, 3280 cm$^{-1}$; MS-FAB (m/z) 431 (M-HSO$_4$)$^+$, 529 MH$^+$; Anal. calcd. for C$_{20}$H$_{32}$N$_8$O$_7$S (528.59), C, 45.4, H, 6.1, N, 21.1, S, 6.1. Found: C, 45.0, H, 6.0, N, 20.7, S, 5.8.

(B)
1-Methyl-4-(1-methyl-4-trimethylammonium-acetamidopyrrole-2-carboxamido)pyrrole-2-carboxamidopropionamidine chloride hydrochloride

A solution of the precursor analogous to that of Example 3(A) (173 mg, 0.35 mmoles) in 10 ml of absolute ethanol was treated with dry hydrogen chloride with cooling. After 2 hours, the solvent was removed in vacuo and the residue dissolved in 10 ml of absolute ethanol and treated with an excess of dry ammonia. After 2 hours at room temperature, the solvent was removed in vacuo and the residue dissolved in 5 ml of isopropyl alcohol; then the product was precipitated with ether. The solid was collected, washed with ether and dried at 100° in vacuo to afford the product 103 mg (59% yield) m.p. 180° (dec); $^1$H-NMR (DMSO-d$_6$): δ1.32 (t, 9H), 2.67 (t, 2H), 3.54 (m, 8H), 3.83 and 3.88 (2s, 6H), 4.32 (s, 2H), 6.96 (d, 1H), 7.01 (d, 1H), 7.21 (d, 1H), 7.30 (d, 1H), 8.28 (t, 1H), 8.80 and 9.10 (2bs, 4H), 10.03 (s, 1H), 11.47 (s, 1H): IR (Nujol): 1376, 1404, 1462, 1531, 1581, 1646, 1684, 3250 cm$^{-1}$; MS-FAB (m/z): 981 (2M-HCl-Cl)$^+$, 473 (M-HCl-Cl)$^+$.

The activities of Examples 3(A) and 3(B) expressed as minimum inhibitory concentration (μg/mL) against vaccinia virus were 20 and 300 respectively illustrating the effects of steric hindrance in DNA binding on reducing agent activity. The larger the terminal group, as demonstrated by compound 3(B), the lesser the activity; hence the terminal group is of a selected size which will maintain DNA sequence bonding desired activity.

EXAMPLE 4

The following compounds of Table 1 are made in accordance with processes similar to Examples 1 and 2. The antiviral properties of the compounds listed in Table 1 were tested to determine the minimum inhibitory concentration to achieve a 50% kill of the viruses in primary rabbit kidney cell cultures.

TABLE 1
ANTIVIRAL PROPERTIES

| m | n | Compound NH$_2$ | | Herpes simplex-1 | Herpes-2 | Vaccinia | Minimal Cytotoxic Conc. (μg/m) |
|---|---|---|---|---|---|---|---|
| 1 | 1 | A = —CH$_2$CH$_2$—C—$^+$NH$_2$, Cl$^-$; | R = —COCH$_2$CO— | 4 | 4 | 0.2 | ≧10 |
| 1 | 1 | A = —CH$_2$CH$_2$—C—$^+$NH$_2$, Cl$^-$; | R = —CO(CH$_2$)$_7$CO | 40 | 40 | 0.2 | ≧100 |
| 1 | 1 | A = —CH$_2$CH$_2$—C—$^+$NH$_2$, Cl$^-$; | R = —CO(CH$_2$)$_6$CO— | 10 | 10 | 0.2 | ≧10 |
| 1 | 2 | A = —CH$_2$CH$_2$—C—$^+$NH$_2$, Cl$^-$; | R = —CO(CH$_2$)$_2$CO— | 4 | 4 | 4 | ≧40 |
| 1 | 1 | A = —CH$_2$CH$_2$—C—$^+$NH$_2$, Cl$^-$; | R = —CO—C$_6$H$_4$—CO— | 10 | 10 | 10 | ≧10 |
| 1 | 1 | A = —CH$_2$CH$_2$—C—$^+$NH$_2$, Cl$^-$; | R = —CO—CH=CH—CO— (trans) | 10 | 10 | 2 | ≧40 |
| | | Distamycin | trans Het = pyrrole | 70 | 70 | 0.2 | 200 |

EXAMPLE 5

Compounds prepared in accordance with the process of this invention are itemized in the following Table 2. The anticancer properties of these compounds were tested to determine the minimum inhibitory concentration of the compounds to achieve 50% cell kill; i.e., ID$_{50}$ as identified in Table 2 is the minimum drug concentration to effect killing of 50% of the cells.

TABLE 2
ANTICANCER PROPERTIES

| m | n | Compound A | R | L1210 | FM3A | RAJI | MOLT/4F |
|---|---|---|---|---|---|---|---|
| 1 | 1 | —CH$_2$CH$_2$C(NH$_2$)(=$^+$NH$_2$), Cl$^-$ | —CO—CH$_2$—CO | 28.5 ± 9.7 | 5.87 ± 2.23 | 3.39 ± 0.69 | 2.85 ± 0.6 |
| 1 | 1 | " | —CO[CH$_2$]$_8$—CO— | 4.21 ± 1.52 | 22.1 ± 11.1 | 3.34 ± 0.44 | 2.97 ± 0.4 |
| 1 | 1 | " | —CO[CH$_2$]$_2$—CO— | 1.2 | 47.2 ± 27.8 | 2.64 ± 2.8 | 33.8 ± 0.9 |
| 1 | 2 | " | —CO[CH$_2$]$_2$—CO— | >100 | 4.29 ± 1.12 | 4.14 ± 8.4 | 100 |
| | | Distamycin Het = pyrrole | | 27.1 ± 4.7 | 30.6 ± 2.4 | 23.7 ± 3.69 | — |

L1210 - murine Leukemia
FM3A - murine mammary tumor
RAJI - human B lymphoblast
MOLT/4F - human T lymphoblast

EXAMPLE 6

The compounds of the following Table 3 were prepared in accordance with processes of this invention. The antileukemic properties of the compounds were tested to determine the minimum inhibitory concentration to achieve 50% cell kill; i.e., ID$_{50}$ in Table 3 is the minimum drug concentration to effect killing of 50% of the cells.

TABLE 3
ANTILEUKEMIC PROPERTIES

| m | n | l | k | R = $(CO)_k(CH_2)_l CO$ A | $ID_{50}$ vs P388 leukemia (μg/ml) |
|---|---|---|---|---|---|
| 1 | 1 | 0 | 0 | $-CH_2CH_2C\begin{smallmatrix}\nearrow NH_2\\ \searrow {}^+NH_2\end{smallmatrix}$, CL$^-$ | 8.0 |
| 1 | 1 | 1 | 1 | " | 0.91 |
| 1 | 1 | 2 | 1 | " | 1.75 |
| 1 | 1 | 3 | 1 | " | 6.4 |
| 1 | 1 | 4 | 1 | " | 1.05 |
| 1 | 1 | 5 | 1 | " | 4.4 |
| 1 | 1 | 6 | 1 | " | 0.70 |
| 1 | 1 | 7 | 1 | " | 0.75 |
| 1 | 1 | 8 | 1 | " | 0.98 |
| | | | | Distamycin | 20 |

25,000 cells per well
72 hours incubation at 37° C.
Het = pyrrole

P388 - murine leukemia
$ID_{50}$ - minimum drug concentration to effect 50% cell kill

EXAMPLE 7

Figure 1:
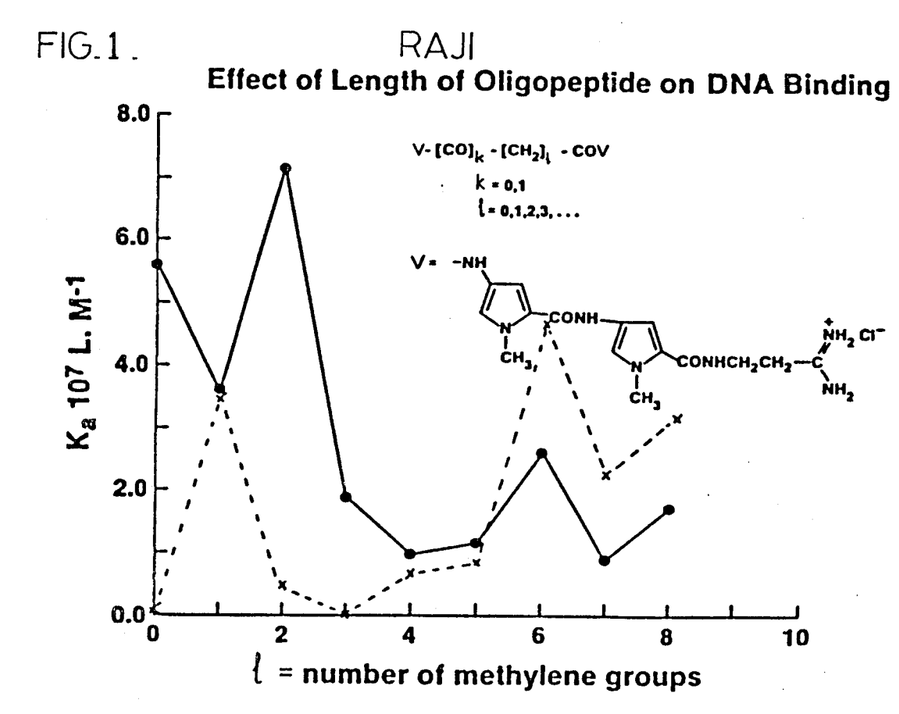
FIG. 1 is a graph plotting the association constant of oligopeptides according to embodiments of this invention representative of the binding affinity of the oligopeptide to DNA vs. the length of the linking unit in the oligopeptide. The dotted line signifies the relative cytotoxicity of these oligopeptides against the tumorous cell lines in culture of MOLT/4F (human T lymphoblast) expressed in ID$_{50}$ values in arbitrary units.
Figure 2:
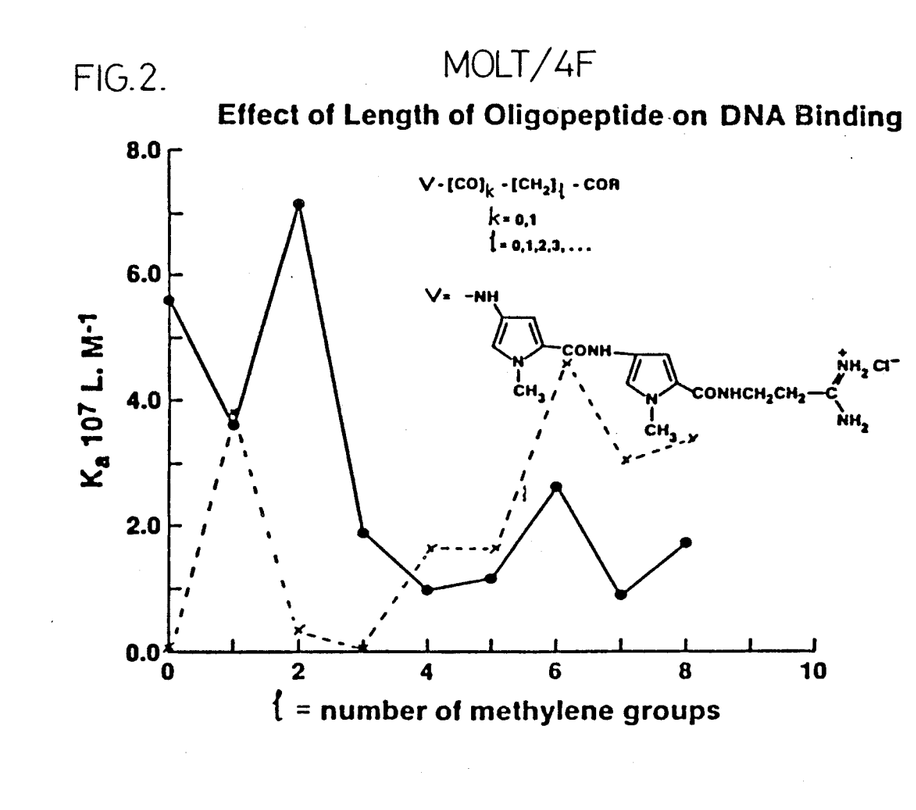
FIG. 2 is a graph plotting the association constant of oligopeptides according to embodiments of this invention representative of the binding affinity of the oligopeptide to DNA vs. the length of the linking unit in the oligopeptide. The dotted line signifies the relative cytotoxicity of these oligopeptides against the tumorous cell lines in culture of Raji (human B lymphoblast) expressed in $ID_{50}$ values in arbitrary units.

FIGS. 1 and 2 are plots of the constant $K_a$ versus the length of the linking group used in linking the pyrrole derivatives. $K_a$ is an association constant of the DNA binding affinity of the oligopeptides in units of $10^7$ L.M$^{-1}$. The solid line of each of FIGS. 1 and 2 shows the variation of the association constant for the following compounds of this invention with the length of the linking group expressed in values of l. The dotted line signifies relative cytotoxicity of these compounds of the invention against similar cell lines in culture. FIG. 1 relates to such acitivity for the cell line MOLT/4F, human T lymphoblast. FIG. 2 related to the tumor cell lines of Raji, human B lymphoblast; all values being expressed in $ID_{50}$ values in arbitrary units. $ID_{50}$ is the minimum drug concentration to effect a 50% cell kill. The general formula for the compounds of this invention as tested in FIGS. 1 and 2 are of formula I, wherein A is represented by:

$$-CH_2-CH_2-O\begin{smallmatrix}\nearrow {}^+NH_2\\ \searrow NH_2\end{smallmatrix}\quad Cl^-$$

m is 1; n is 1 and Het is pyrrole, R is represented by the formula $CO_k-(CH_2)_l-CO$ where l is equal to 0, 1, 2, 3, 4, 5, 6, 7 or 8 and k is equal to 0 or 1. From the results of FIGS. 1 and 2, it is apparent that affinity for binding with DNA is affected by increasing the length of the linking group but not to an adverse extent, because cytotoxicity of the compounds with the longer linking groups is maintained, as exemplified by the dotted lines.

Although preferred embodiment of the invention have been described herein in detail, it will be understood by those skilled in the art that variations may be made thereto without departing from the spirit of the invention or the scope of the appended claims.

The embodiments of the invention in which an exclusive property or privilege is claimed are defined as follows:

1. A compound of the formula I:

$$\text{A-(NHCO)}_m\text{-Het-(NHCO-Het)}_n\text{-NH-R-NH-(Het-CONH)}_n\text{-Het-(CONH)}_m\text{-A}$$

wherein:

A is a moiety bearing a positive charge and of a size which does not inhibit binding of said compounds to deoxyribonucleic acid sequences;

R is a moiety derived from a residue of carbonic acid or a residue of a dicarboxylic acid selected from the group consisting of:

(i) a residue of a dicarboxylic acid of the formula -CO-$C_pH_{2p}$-CO-where p equals 1 to 16;

(ii) a residue of an unsaturated aliphatic dicarboxylic acid of the formula -CO-$C_pH_{2p-2}$-CO- where p equals 2 to 16;

(iii) a residue of an aromatic dicarboxylic acid;

(iv) a residue of a cycloalkane dicarboxylic acid of the formula -CO-$C_pH_{2p-2}$-CO- where p equals 3 to 7, and (v) a residue of a cycloalkene dicarboxylic acid of the formula -CO-$C_pH_{2p-4}$-CO- where p equals 5 to 7;

Het is a five-membered heterocyclic moiety selected from the group consisting of a pyrrole, an imidazole, a triazole, a pyrazole, a thiazole, a thiophene, a furan and an oxazole;

n is 1, 2, or 3; and m is 0 or 1 and salts thereof.

2. A compound of claim 1 wherein A is a moiety selected from the group consisting of an amidine, a guanidine, secondary ammonium salts, tertiary ammonium salts, quaternary ammonium salts, sulfonium salts and phosphonium salts.

3. A compound of claim 1 wherein Het is an N-alkyl pyrrole with said alkyl group consisting of 1 to 6 carbon atoms.

4. A compound of claim 1 wherein Het is an N-alkyl imidazole with said alkyl group consisting of 1 to 6 carbon atoms.

5. A compound of claim 1, wherein Het is an N-alkyl pyrazole with said alkyl group consisting of 1 to 6 carbon atoms.

6. A compound of claim 1 wherein Het is an N-alkyl triazole with said alkyl group consisting of 1 to 6 carbon atoms.

7. A compound of claim 1, wherein Het in said formula I is at least two different moieties selected from said group.

8. A compound of claim 7, wherein at least one Het moiety is an N-alkyl pyrrole which has said alkyl group of 1 to 6 carbon atoms.

9. A compound of claim 7, wherein at least one Het moiety is an N-alkyl imidazole which has said alkyl group of 1 to 6 carbon atoms.

10. A compound of claim 7, wherein at least one Het moiety is an N-alkyl triazole which has said alkyl group of 1 to 6 carbon atoms.

11. A compound of claim 7, wherein at least one Het moiety is an N-alkyl pyrazole which has said alkyl group of 1 to 6 carbon atoms.

12. A compound of claim 1 wherein R is $$-\overset{\overset{\text{O}}{\|}}{\text{C}}-.$$

13. A compound of claim 1, wherein R is a residue of a dicarboxylic acid of the formula -CO-$C_pH_{2p}$-CO- where p equals 1 to 16.

14. A compound of claim 1, wherein R is a residue of an unsaturated aliphatic dicarboxylic acid of the formula —CO—$C_pH_{2p-2}$—CO— where p equals 2 to 15. A compound of claim 1, wherein R is a residue of an aromatic dicarboxylic acid.

16. A compound of claim 1, wherein R is a residue of a cycloalkane dicarboxylic acid of the formula —CO—$C_pH_{2p-2}$—CO— where p equals 3 to 7.

17. A compound of claim 1, wherein R is a residue of a cycloalkene dicarboxylic acid of the formula —CO—$C_pH_{2p-4}$—CO— where p equals 5 to 7.

18. A compound of claim 2, wherein A is an amidine of the formula:

where p equals 0 to 5 and X is —H; —OH; —$NH_2$; —$CH_3$; —$C_2H_5$; —$C_3H_7$.

19. A compound of claim 2, wherein A is an amidine in which nitrogen atoms are in a five-membered cyclic structure.

20. A compound of claim 2, wherein A is guanidine of the formula:

where p equals 0 to 5 and X equals —H; —OH; —$NH_2$; —$CH_3$; —$C_2H_5$; —$C_3H_7$.

21. A compound of claim 2 wherein A is a quaternary, tertiary or secondary ammonium salt of the formula:

-$C_pH_{2p}$-$^+NH_q[Z]X_{(3-q)}$ wherein p equals 0 to 5 and q equals 0 to 3 and X is an alkyl or alkenyl group consisting of 1 to 3 carbon atoms.

22. A compound of claim 2 wherein A is a sulfonium salt of the formula:

—$C_p$—$H_{2p}$—SXY wherein p equals 0 to 5 and X and Y are alkyl or alkenyl groups of 1 to 3 carbon atoms.

23. A compound of claim 18, wherein Het is pyrrole and m is 1.

24. A compound of claim 23, wherein A is

25. A compound of claim 24, wherein R is -CO($CH_2$)$_l$ CO- and l equals 0 to 16.

26. A compound of claim 25, wherein l is 2, and n is 1.

27. A process for producing a compound of the formula:

A-(NHCO)$_m$-Het-(NHCO-Het)$_n$-NH-R-NH-(Het-CONH)$_n$-Het-(CONH)$_m$-A wherein:
A is a moiety bearing a positive charge and of a size which does not inhibit binding of said compounds to deoxyribonucleic acid sequences;
R is a moiety derived from a dicarboxylic acid and selected from group consisting of:
 (i) a residue of a dicarboxylic acid of the formula —CO—$C_pH_{2p}$—CO— where p equals 1 to 16;
 (ii) a residue of an unsaturated aliphatic dicarboxylic acid of the formula —CO—$C_pH_{2p-2}$—CO— where p equals 2 to 16;
 (iii) a residue of an aromatic dicarboxylic acid;
 (iv) a residue of a cycloalkane dicarboxylic acid of the formula —CO—$C_pH_{2p-2}$—CO— where p equals 3 to 7, and
 (v) a residue of a cycloalkene dicarboxylic acid of the formula —CO—$C_pH_{2p-4}$—CO— where p equals 5 to 7;
Het is a five-membered heterocyclic moiety selected from the group consisting of a pyrrole, an imidazole, a triazole, a pyrazole, a thiazole, a thiophene, a furan and an oxazole;
n is 1, 2, or 3; and
m is 0 or 1 and salts thereof;
said process comprising reacting a compound of the formula:

B-(NHCO)$_m$-Het-(NHCO-Het)$_n$-$NH_2$ wherein m and n are as defined above, and
B is the same as A or is a group containing nitrile, halogen or sulfide substituent;
with a dicarboxylic acid of the formula:

X-R-X wherein R is as defined above and
X is halogen or imidazolide
and converting B to A to form said moiety bearing a positive charge by selecting one of the following reaction conditions:
 (i) reduction of nitrile to a primary amide followed by protonation;
 (ii) displacement of said halogen with an amine; or
 (iii) alkylation of said sulfide with an alkyl halide.

28. A process of claim 27, wherein X is a group Cl-$C_pH_{2p}$, p being equal 0 to 5.

29. A process of claim 27, wherein B is CN-$C_pH_{2p}$-, converting B to an amidine hydrochloride salt moiety of by further reacting substituent B with hydrochloric acid in the presence of an alcohol and subsequent treatment with ammonia, p being equal 0 to 5.

30. A process of claim 27, wherein B is Cl-$C_pH_{2p}$-, converting B to an ammonium salt of $X_{(3-q)}+NH_q$-$C_pH_{2p}$ by further reacting B with $NH_qX_{(3-q)}$, p being equal to 0 to 5, q being equal 0 to 3, and X being an alkyl or alkenyl group having 1 to 3 carbon atoms.

31. A process of claim 27, wherein B is $XS\text{-}C_pH_{2p}\text{-}$, converting B to a sulfonium salt of $XYS^+\text{-}C_pH_{2p}\text{-}$ by further reacting B with Y(hal), p being equal 0 to 5, and X and Y being selected from the group consisting of an alkyl and an alkenyl group having 1 to 3 carbon atoms.

32. A process of claim 27, wherein A is selected from the group consisting of an amidine, a guanidine, secondary ammonium salts, tertiary ammonium salts, quaternary ammonium salts, sulfonium salts and phosphonium salts.

33. A process of claim 29 for preparing a compound wherein Het is pyrrole and m is 1.

34. A process of claim 33 for preparing a compound wherein a hydrochloride salt of A is and B is $CN\text{-}C_pH_{2p}\text{-}$ wherein p is 2.

35. A process of claim 31 for preparing a compound wherein R is $-CO(CH_2)_{[1]l}CO-$ and l equals 0 to 16.

36. A process of claim 27, wherein B is a guanidine derivative of the formula:

and p equals 0 to 5.

37. A process of claim 27, wherein B is an amidine derivative of the formula:

and p equals 0 to 5.

* * * * *

UNITED STATES PATENT AND TRADEMARK OFFICE
CERTIFICATE OF CORRECTION

PATENT NO. : 4,912,199  Page 1 of 3
DATED : March 27, 1990
INVENTOR(S) : J. WILLIAM LOWN & KRYZYSTOF KROWICKI It is certified that error appears in the above-indentified patent and that said Letters Patent is hereby corrected as shown below:

Column 4, line 61, "where 1 may range" should read --where $l$ may range--.

Column 6, last line before "D - Preparation of Sulfonium Salts", change

"$[X_{(3-q)}{}^{+}NH_q—C_pH_{2p}—(NHCO)_m—Het—(NHCO—Het)—NH_2—R]$" to read

--$[X_{(3-q)}{}^{+}NH_q—C_pH_{2p}—(NHCO)_m—Het—(NHCO—Het)_n—NH_2—R]$--.

Column 7, line 60, insert after "3.60 (m, " --2H), 3.83 (s, 6H),--.

Table 1, in the first compound, both m and n are both 1.

Table 3, fourth column, the heading should be --$l$--.

Column 11, line 36, "values of 1" should read --values of $l$--;

line 54, "formula $CO_k—(CH_2)_1—CO$ where 1 is equal" should read --formula $CO_k—(CH_2)_l—CO$ where $l$ is equal--.

UNITED STATES PATENT AND TRADEMARK OFFICE
CERTIFICATE OF CORRECTION

PATENT NO. : 4,912,199
DATED : March 27, 1990
INVENTOR(S) : J. WILLIAM LOWN & KRZYSZTOF KROWICKI It is certified that error appears in the above-indentified patent and that said Letters Patent is hereby corrected as shown below:

Column 13, line 6, Claim 14, line 3, after "2 to" add --16--;

line 42, Claim 21, line 4, "-$C_pH_{2p}$+$NH_q[Z]]X(3-q)$" should read -- -$C_pH_{2p}$+$NH_qX(3-q)$--;

line 62, Claim 25, line 2, "—$CO(CH_2)_lCO$- and l equals" should read -- —$CO(CH_2)_lCO$- and $l$ equals--;

line 63, Claim 26, line 1, "l is 2" should read --$l$ is 2--.

Column 14, line 9, Claim 27, line 10, after "from" insert --the--;

UNITED STATES PATENT AND TRADEMARK OFFICE
CERTIFICATE OF CORRECTION

PATENT NO.    : 4,912,199                              Page 3 of 3
DATED         : March 27, 1990
INVENTOR(S)   : J.WILLIAM LOWN & KRYZYSTOF KROWICKI It is certified that error appears in the above-indentified patent and that said Letters Patent is hereby corrected as shown below:

Column 16, line 2, Claim 35, line 2, "R is $-CO(CH_2)_{m}CO-$ and l equals" should read -- R is $-CO(CH_2)_{l}CO-$ and $l$ equals--.

Signed and Sealed this

Twenty-second Day of March, 1994

Attest:

BRUCE LEHMAN

*Attesting Officer*     *Commissioner of Patents and Trademarks*